US008551292B2

(12) United States Patent
Goto et al.

(10) Patent No.: US 8,551,292 B2
(45) Date of Patent: Oct. 8, 2013

(54) METHODS FOR DETERMINING THE DEGREE OF DEPOSITION OF CONTAMINANTS

(75) Inventors: Shisei Goto, Tokyo (JP); Yasunobu Ooka, Tokyo (JP); Kosuke Okamoto, Tokyo (JP)

(73) Assignee: Nippon Paper Industries Co., Ltd., Tokyo (JP)

( * ) Notice: Subject to any disclaimer, the term of this patent is extended or adjusted under 35 U.S.C. 154(b) by 0 days.

(21) Appl. No.: 13/501,791

(22) PCT Filed: Oct. 13, 2010

(86) PCT No.: PCT/JP2010/067919
§ 371 (c)(1),
(2), (4) Date: Apr. 13, 2012

(87) PCT Pub. No.: WO2011/046130
PCT Pub. Date: Apr. 21, 2011

(65) Prior Publication Data
US 2012/0211190 A1 Aug. 23, 2012

(30) Foreign Application Priority Data

Oct. 14, 2009 (JP) .................................. 2009-237759

(51) Int. Cl.
*D21F 11/00* (2006.01)
(52) U.S. Cl.
USPC ......................................... 162/198; 162/199
(58) Field of Classification Search
USPC .................... 162/198, 199; 356/72
See application file for complete search history.

(56) References Cited

U.S. PATENT DOCUMENTS

| | | | |
|---|---|---|---|
| 2002/0096269 A1* | 7/2002 | Bouchette et al. ................. | 162/4 |
| 2002/0129909 A1* | 9/2002 | de Jong et al. ..................... | 162/4 |
| 2004/0065419 A1* | 4/2004 | Lasmarias et al. ................. | 162/5 |
| 2006/0281191 A1* | 12/2006 | Duggirala et al. ............ | 436/178 |
| 2007/0062662 A1* | 3/2007 | Gray et al. ..................... | 162/199 |
| 2009/0056897 A1* | 3/2009 | Shevchenko et al. ......... | 162/198 |
| 2009/0065440 A1* | 3/2009 | Hicks et al. .................... | 210/696 |
| 2009/0084510 A1* | 4/2009 | Perry et al. ....................... | 162/49 |
| 2009/0141963 A1* | 6/2009 | Laurint et al. ................. | 382/141 |
| 2009/0314445 A1* | 12/2009 | Shevchenko et al. ......... | 162/161 |

FOREIGN PATENT DOCUMENTS

| | | |
|---|---|---|
| JP | 2001-013054 | 1/2001 |
| JP | 2006-523450 | 10/2006 |
| JP | 2007-271545 | 10/2007 |
| JP | 2009-503272 | 1/2009 |
| JP | 2009-198414 | 9/2009 |
| WO | 2004/094656 | 11/2004 |
| WO | 2006/135612 | 12/2006 |
| WO | 2008/132487 | 11/2008 |

OTHER PUBLICATIONS

Lee, H.L. et al., Quantification of macro and micro stickies and their control by flotation in OCC recycling process, Appita Journal, 2006, vol. 59, No. 1, pp. 31-36.
Doshi, M. et al., Comparison of microstickies measurement methods. Part I: Sample preparation and Measurement methods, Progress in Paper Recycling, 2003, vol. 12, No. 4, pp. 35-42.
Doshi, M. et al., Comparison of microstickies measurement methods. Part II: Results and discussion, Progress in Paper Recycling, 2003, vol. 13, No. 1, pp. 44-53.
International Search Report for PCT/JP2010/067919, dated Nov. 30, 2010.

* cited by examiner

*Primary Examiner* — Mark Halpern
(74) *Attorney, Agent, or Firm* — Roylance, Abrams, Berdo & Goodman, L.L.P.

(57) ABSTRACT

Herein provided are methods for determining deposition of contaminants significantly influencing machine runnability or product quality in manufacturing processes of pulp and paper, especially determining the degree of deposition and the morphology of deposits of sticky contaminants or pitch and for evaluating the effect of chemicals for reducing deposition. In a manufacturing process of pulp and paper is used a method comprising: determining the degree of deposition of a contaminant from a liquid or slurry on a quartz crystal oscillator; and quantifying the morphology of deposits on the surface of the quartz crystal oscillator by image analysis. Further, a method comprising adding a chemical for reducing deposition to the liquid or slurry and then quantifying the degree of deposition and the morphology of deposits is used to evaluate the effect of the chemical.

11 Claims, 8 Drawing Sheets

METHODS FOR DETERMINING THE DEGREE OF DEPOSITION OF CONTAMINANTS

This application is a 371 of PCT/JP2010/067919 filed 13 Oct. 2010.

TECHNICAL FIELD

The present invention relates to methods for determining the degree of deposition of contaminants occurring at various stages of manufacturing processes of pulp and paper. More specifically, it relates to methods by which problems in operation and quality caused by deposition of contaminants can be detected and addressed early by continuously determining the degree of deposition of contaminants from information obtained from a microbalance having a quartz crystal oscillator placed at various stages of manufacturing processes of pulp and paper and quantifying the morphology of deposits on the surface of the quartz crystal oscillator by image analysis.

BACKGROUND ART

Manufacturing processes of pulp and paper often involve deposition of contaminants, including among others scales; pitch consisting of resin acids or fatty acids derived from wood or latex derived from coating layers; sticky contaminants derived from adhesive materials (acrylic, vinyl acetate, hot-melt and the like adhesive materials such as adhesive tapes, glues for binding magazines, plastic tapes, etc.) contained in waste paper; and chemicals such as sizing agents or starch added in the processes; and these contaminants adhere to wires, canvas, felt or the like to cause problems including decreased paper machine runnability such as dehydration failure or paper breaks and product quality loss such as paper surface defects.

These pitch and sticky contaminants are dispersed as very small particles or colloids in slurries during the papermaking process, but destabilized from the dispersed state by high shear stress, rapid pH change, addition of fixing agents such as aluminum sulfate or the like so that they are deposited or agglomerated/coalesced by binding to impurity ions or inorganic or organic matters. Coalesced pitch is deposited on pipes, wires or the like or redeposited on pulp or paper to cause quality loss due to defects in paper and paper breaks inducing productivity loss and the like.

Especially, the recent trends toward closed processes for environmental consideration have amplified and complicated pitch problems. Moreover, an increased use of recycled pulp for environmental consideration and cost saving has tended to introduce higher amounts of pitch or sticky contaminants into manufacturing processes of pulp and paper and worsened problems with these contaminants.

To address the problems with pitch or sticky contaminants described above, it is very important to know the numerical level or characteristics of the pitch or sticky contaminants introduced into manufacturing processes of pulp and paper, and some methods for evaluating pitch and coalesced sticky contaminants that can be eliminated by a screen having a slit width of 100 μm have been currently established and have been known to provide reliable data.

However, it is very difficult to evaluate small sticky contaminants due to their properties, and no method has been established though many reports exist. For example, an approach to evaluate small sticky contaminants relies on organic solvent extraction. However, this method determines the amounts of not only sticky contaminants but also oils derived from ink vehicles or other non-sticky solvent extracts derived from surfactants.

It cannot be said that the amounts of sticky contaminants are precisely determined by such an extraction method, as shown from the analytical results of adhesive-derived components occupying solvent extracts of deposits in an actual manufacturing process in non-patent document 1 reporting that adhesives represent only slightly less than about 5% of the extracts, for example. In addition, this method requires a very long time including extraction time (non-patent document 1).

Other methods have also been proposed by determining the amounts of deposits on a hydrophobic film or a metal wire, or determining COD or TOC or the like, but these methods are insufficient for determining small sticky contaminants because the amounts of deposits are very small so that the former method introduces a significant error from other materials such as fibers while the latter method fails to evaluate deposition by COD or TOC (non-patent documents 2 and 3).

Based on the recently evolved techniques for determining deposition of substances in water using a quartz crystal oscillator, methods for determining the degree of deposition of contaminants (patent document 1) and methods for monitoring deposition of organic or inorganic matters (patent documents 2 and 3) have been proposed. These methods allow accurate quantification of very small amounts so that the amounts of the pitch or small sticky contaminants deposited or sedimented can be precisely determined.

CITATION LIST

Patent Documents

Patent document 1: JPA No. 2007-271545
Patent document 2: JPA No. 2009-503272
Patent document 3: JPA No. 2006-523450

Non-Patent Documents

Non-patent document 1: Hak Lae Lee, Jong Min Kim, Quantification of Macro and Micro Stickies and Their Control by Flotation in OCC Recycling Process, Appita Journal, Vol. 59, No. 1, 31-36, 2006.
Non-patent document 2: Mahendra R. Doshi et. al, Comparison of Microstickies Measurement Methods Part I, Progress in Paper Recycling, Vol. 12, No. 4, 35-42, 2003.
Non-patent document 3: Mahendra R. Doshi et. al, Comparison of Microstickies Measurement Methods Part II, Progress in Paper Recycling, Vol. 13, No. 1, 44-53, 2003.

DISCLOSURE OF INVENTION

Technical Problems

However, no information about the morphology of substances deposited or sedimented could not be obtained by the methods of patent documents 2 and 3 above.

On the other hand, it has been clarified that the morphology of contaminants deposited or sedimented during the papermaking process changes by adding cationic low molecular weight polymers called coagulants or enzymes or pacification agents as a strategy against pitch or small sticky contaminants and that contaminants in more finely dispersed state are preferable to agglomerated/coalesced state even if they are deposited or sedimented in the same amounts because contaminants of larger than 100 μm often pierce papers having a thickness of 100 μm or less to cause problems such as paper breaks or product defects.

Thus, the present invention provides methods for determining deposition of contaminants greatly influencing paper machine runnability or product quality in manufacturing processes of pulp and paper, especially the degree of deposition and the morphology of deposits of sticky contaminants or pitch and for evaluating the effect of deposition-reducing chemicals.

Technical Solution

Bearing in mind that microbalances having a quartz crystal oscillator are capable of weight measurements on a molecular level as well as real-time and therefore, continuous measurements, we devoted our efforts to studies to acquire an image of deposits on the surface of a quartz crystal oscillator and, as a result, we found that when a liquid or slurry is contacted onto a quartz crystal oscillator to determine the degree of deposition, the morphology of deposits can be quantified by image analysis on the surface of the oscillator. Further, we found that the effect of a deposition-reducing chemical can be evaluated by quantifying the degree of deposition and the morphology of deposits before and after the chemical is added.

In a preferred embodiment, the present invention provides a method for determining deposition of a contaminant from a liquid or slurry in a manufacturing process of pulp and paper, characterized in that the method comprises: using a microbalance having a quartz crystal oscillator to determine the degree of deposition of the contaminant from the liquid or slurry on the quartz crystal oscillator; and quantifying the morphology of deposits on the surface of the quartz crystal oscillator by image analysis.

Moreover, the present invention further comprises: adding a chemical for reducing deposition of the contaminant to the liquid or slurry; using a microbalance having a quartz crystal oscillator to determine the degree of deposition of the contaminant on the surface of the quartz crystal oscillator from the liquid or slurry after the chemical has been added; and comparing the degree of deposition of the contaminant in the presence of the chemical with the degree of deposition of the contaminant in the absence of the chemical to evaluate the effect of the chemical; whereby the effect of the chemical for reducing deposition from the liquid or slurry in the manufacturing process of pulp and paper can be evaluated.

Advantageous Effects of Invention

According to the present invention, the degree of deposition of contaminants such as sticky contaminants or pitch occurring in manufacturing processes of pulp and paper can be precisely determined. Further, the morphology of deposits can be quantified by image analysis to determine if the contaminants are dispersed and fixed to resist deposit problems such as paper breaks or defects or the contaminants are agglomerated/coalesced and fixed to cause deposit problems.

Figure 1:
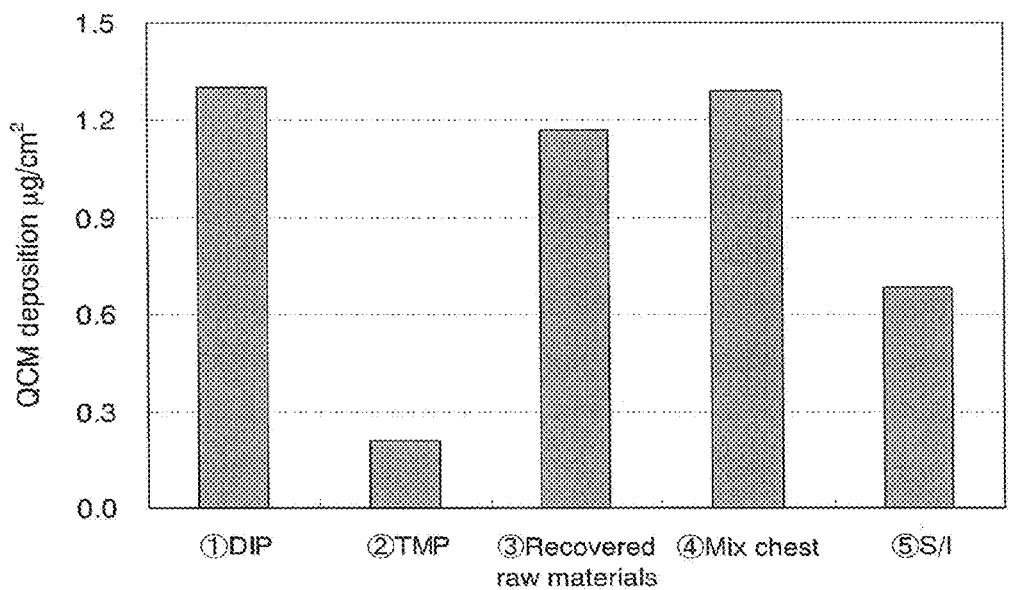
FIG. 1 is a graph showing the degree of deposition of contaminants on a quartz crystal oscillator at various process stages.

DESCRIPTION OF EMBODIMENT (Manufacturing Processes of Pulp and Paper)

As used herein, manufacturing processes of pulp refer to processes by which pulp (cellulose) is extracted from chips, logs, waste paper or dry sheets. Further, they include liquids added to these materials such as industrial water or treated industrial effluent or white water used before pulp is extracted and processes for recycling/recovering such liquids. Specifically, they include white water, service water, industrial grade water, recycled service water, industrial water, washed water from washers, drain water from drainage systems (e.g., DNT washers, extractors, screw presses, etc.), froth or rejects from floatators, scum and accepts from dissolved air flotation equipment, cloudy water from white water recovery filters, clear white water, shower water, wash water of felt or the like and diluted water of raw materials produced or used in manufacturing processes of pulp and/or paper; or these waters having undergone a separation process such as flotation separation, foam separation, precipitation, membrane separation, centrifugation, flocculation, etc.

Pups include chemical pulps (softwood bleached kraft pulp (NBKP) or unbleached kraft pulp (NUKP), hardwood bleached haft pulp (LBKP) or unbleached kraft pulp (LUKP), etc.), mechanical pulps (groundwood pulp (GP), thermomechanical pulp (TMP), chemithermomechanical pulp (CTMP), etc.), recycled pulps such as deinked pulp (DIP), etc. The present invention can be applied to these pulps alone or a mixture thereof in any ratios.

As used herein, manufacturing processes of paper refer to processes by which pulp is converted into sheets, including any processes such as wet-end process, pressing process, dryer process, calendering process, drain process and processes for treating these service waters. As used herein, the wet-end process may be the process by which paper is made using a known paper machine such as, but not limited to, a Fourdrinier paper machine, twin wire paper machine or cylinder paper machine. The paper may be a single- or multi-layer paper. The process for treating service water includes the liquids used before pulp is extracted and processes for recycling/treating such liquids.

Further, the stock may contain fillers, and known fillers can be used alone or in combination, including inorganic fillers such as precipitated calcium carbonate, ground calcium carbonate, clay, calcined kaolin, delaminated kaolin, white carbon, magnesium carbonate, barium carbonate, titanium dioxide, zinc oxide, silicon oxide, amorphous silica, calcium carbonate-silica complexes, aluminum hydroxide, calcium hydroxide, magnesium hydroxide and zinc hydroxide; organic fillers such as urea-formalin resins, polystyrene resins, phenol resins and hollow microparticles; and recycled fillers obtained by burning the sludge produced in a process for recycling waste paper or a process for preparing paper and those recycled fillers coated on their surfaces with calcium carbonate, silica, aluminum hydroxide or the like. Additionally, aluminum sulfate, sizing agents, paper strength enhancers, retention aids, freeness improvers, colorants, dyes, antifoaming agents and the like can also be contained as appropriate.

The types of papers prepared by the manufacturing processes of paper in the present invention include, but not limited to, printing papers and newsprint papers as well as specialty papers for communication, converting papers, sanitary papers, papers for paper containers, papers for wrapping materials, etc. Specialty papers for communication more specifically include electrophotographic transfer paper, ink jet printing paper, business form printing paper, heat-sensitive printing paper, pressure-sensitive printing paper, etc. Converting papers more specifically include base paper for casting paper, base paper for wall paper, base paper for release paper, base paper for laminated board, base paper for molding, etc. Sanitary papers more specifically include facial tissue, toilet tissue, paper towels, etc. Paperboards such as liners and base paper for corrugated fiberboard are also included. These papers may be coated with organic or inorganic materials on their surfaces.

(Microbalance Having a Quartz Crystal Oscillator)

As used herein, a microbalance having a quartz crystal oscillator may be any instrument capable of measuring small weight changes occurring on the surface of a quartz crystal oscillator by taking advantage of the piezoelectric effect of the oscillator. The microbalance having a quartz crystal oscillator is a molecular interaction analyzer (model: QCM-D300) from Q-sence or the like, for example. The measuring principle of this analyzer is as follows.

When an AC voltage is applied across a quartz crystal oscillator, the crystal quartz is distorted. At that time, the quartz oscillates very regularly. If a sample is deposited on the surface of the quartz crystal oscillator, the frequency changes. The mass of the sample deposited on the surface of the quartz crystal oscillator can be determined because the frequency shift is proportional to the mass of membranes deposited.

Specifically, the frequency shift ($\Delta f$) is measured by the analyzer above. The frequency shift $\Delta f$ can be said to represent the weight of a contaminant in a wet state deposited on the surface of the quartz crystal oscillator because the relationship between $\Delta f$ and the weight change $\Delta m$ in a wet state is defined by equation 1 below:

$$\Delta f = \text{Constant} \times \Delta m \quad \text{(equation 1)}$$

Further, $\Delta f$ can be rewritten as the weight change ($\Delta m$) of the contaminant in a wet state deposited on the surface of the quartz crystal oscillator by using the equation of Sauerbrey shown below (equation 2 below). It should be noted that $\Delta f$ used in equation 2 is each of the $\Delta f$ values measured at 4-step frequencies of 5, 15, 25 and 35 MHz automatically switched in the above analyzer and divided by 1, 3, 5 and 7, respectively (converted into the values at 5 MHz).

$$\Delta m = -17.7 \, (\text{ng} \cdot \text{cm}^{-2} \cdot \text{Hz}^{-1}) \cdot \Delta f \, (\text{Hz}) \quad \text{(equation 2)}$$

The liquid or slurry analyzed may have a solids content of 5% or less. Samples containing long fibers or large particle size contaminants are preferably analyzed after they are pretreated. Pretreatment methods may include conventional screening, filtration and the like, but any method can be used so far as a filtrate having a solids content of 5% by weight or less and a long pulp fiber content of 50% by weight or less relative to the total solids can be collected. As used herein, a long pulp fiber content refers to pulp fibers retained on a 150-mesh screen.

(Quartz Crystal Oscillator)

In the present invention, the surface of the quartz crystal oscillator may be coated with a heavy metal such as gold, platinum, silver, lead, iron titanium or cadmium and/or a compound such as stainless steel or silicon dioxide. Further, the surface may be coated with a material having a solid surface free energy of 75 mJ/m$^2$ or less. Alternatively, the oscillator can be used after such a material as a water-soluble protein, polymer electrolyte or surfactant has been adsorbed to the surface in a liquid.

When the target of analysis is the pitch or sticky contaminant described below, the quartz crystal oscillator is preferably coated with a hydrophobic material. This means that the surface of the quartz crystal oscillator is coated to promote deposition of hydrophobic substances such as pitch components in a process onto the surface of the quartz crystal oscillator. Hydrophobic materials used for coating include organic materials having a solid surface free energy of 15-50 mJ/m$^2$, preferably 30-40 mJ/m$^2$ to show good adhesion to pitch components, e.g., polystyrene resins, polyethylene resins, polypropylene resins, etc., but are not specifically limited so far as they show hydrophobicity.

Further, two or more quartz crystal oscillators coated with different materials on their surfaces can be used to determine deposition of a contaminant from a liquid or slurry. In this case, a quartz crystal oscillator coated with a material having a surface free energy of 40 mJ/m$^2$ or less and a quartz crystal oscillator coated with a hydrophilic organic material having a surface free energy of more than 40 mJ/m$^2$ or an inorganic material such as stainless steel can also be used to compare susceptibility to deposition of the contaminant on the different surfaces.

(Deposition of Contaminants)

As used herein, contaminants collectively refer to substances produced in manufacturing processes of pulp and paper and adversely influencing product quality and runnability. For example, they refer to metal salt scales such as calcium oxalate, calcium sulfate, barium sulfate, calcium carbonate, aluminum silicate; natural pitch consisting of triglycerides derived from mechanical pulp or resin components such as abietic acid; white pitch consisting of additive chemicals used in manufacturing processes of pulp and paper such as sizing agents or starch, paper softeners and density-reducing agents and hydrophobic substances based on organic matters such as latex derived from coating layers and the like; and sticky contaminants such as acrylic, vinyl acetate, hot-melt and the like adhesive materials such as adhesives, adhesive tapes, glues for binding magazines, plastic tapes and the like derived from waste paper.

As used herein, deposition of a contaminant means that the contaminant is deposited and sedimented on any materials such as pipes, wires, equipment and the like in manufacturing processes of pulp and paper. Deposition includes, for example, not only direct deposition of an adhesive matter but also precipitation of a substance suspended in water and destabilization of a dispersed substance by pH shock or temperature change to form a deposit. In actual manufacturing processes of pulp and paper, the contaminant is deposited along with ashes such as fillers or pigments and small fibers. Especially when the contaminant is deposited on the surfaces of ashes, a large deposit including the ashes is formed, and therefore, contaminants as used herein also include complexes containing the fillers or the like.

Further, the degree of deposition refers to the amount or speed of a substance deposited on a quartz crystal oscillator sensor in a predetermined period.

(Quantification of the Morphology of Deposits)

The morphology of a contaminant deposited on the surface of a quartz crystal oscillator can be quantified by acquiring an image of it by using a microscope and calculating the area ratio or average particle size of deposits, or the area ratio of large deposits or its ratio to the total area by image analysis on the basis of the image. For example, information associated with problems of pitch/sticky contaminants in a paper machine can be obtained by acquiring an image of the surface of a quartz crystal oscillator at 400× magnification using Ultra-deep Color 3D Profile Measuring Microscope (VK9500) from Keyence Corporation and dividing the area of deposits having a predetermined particle size or more by the total measured area using a particle analysis application (VK-H1V9) from the same manufacturer to quantify the area ratio of coalesced deposits.

According to the present invention, the operating state of a paper machine can be exactly known because relatively small deposited contaminants can be precisely measured and the morphology of deposits can be quantified by image analysis. Generally, contaminants exceeding 100 µm pierce papers having a thickness of 100 µm or less to cause problems such as paper breaks or product defects, but the tendency of contaminants to be agglomerated/coalesced in a papermaking system can be rapidly detected by determining the ratio of deposits having a predetermined size or more according to the present invention. In the present invention, the ratio of deposits having a predetermined particle size or more is preferably quantified by image analysis of deposits, and the size of deposits here can be determined as appropriate. For example, the area ratio of deposits having a particle size of a predetermined value or more between 3-20 µm can be determined and exploited for the operation control of a papermaking system. The morphology of deposits can be preferably quantified by determining the area ratio of deposits having a particle size of a predetermined value or more between 3-15 µm, more preferably a particle size of a predetermined value or more between 3-10 µm, even more preferably a particle size of a predetermined value or more between 5-8 µm, most preferably a particle size of about 6 µm or more. Generally, when a chemical for reducing deposition of contaminants is added to a papermaking system, the contaminants may be agglomerated into larger particles or decomposed/disaggregated into smaller particles to undergo morphological changes, but such morphological changes of contaminants can be exactly traced according to the present invention.

(On-Line Measurements)

For on-line measurements in the present invention, a filtrate can be obtained by using e.g., a drainage system such as a filtrate collector (REX-100S-ST) from Koei Industry Co., Ltd., but any system can be used that is capable of adjusting the solids content of a liquid or slurry to 5% by weight or less, preferably 1% by weight or less and the long pulp fiber content in the filtrate to 50% by weight or less relative to the total solids.

Figure 11:
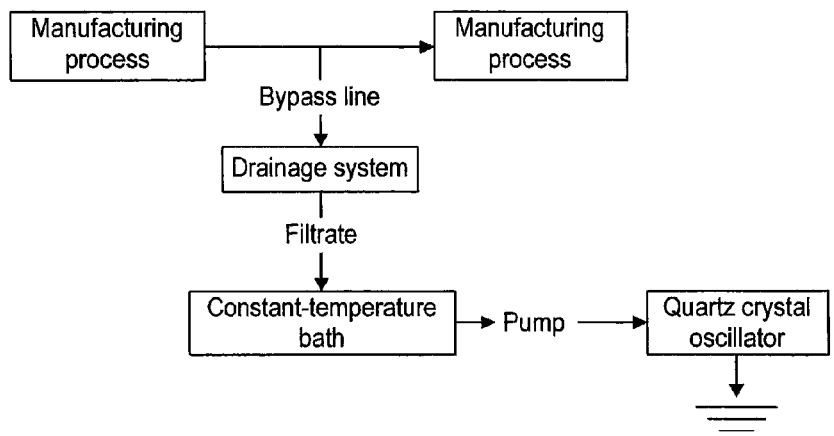
FIG. 11 is a flow chart of an on-line measurement of the present invention incorporating an on-line drainage system.
Figure 12:
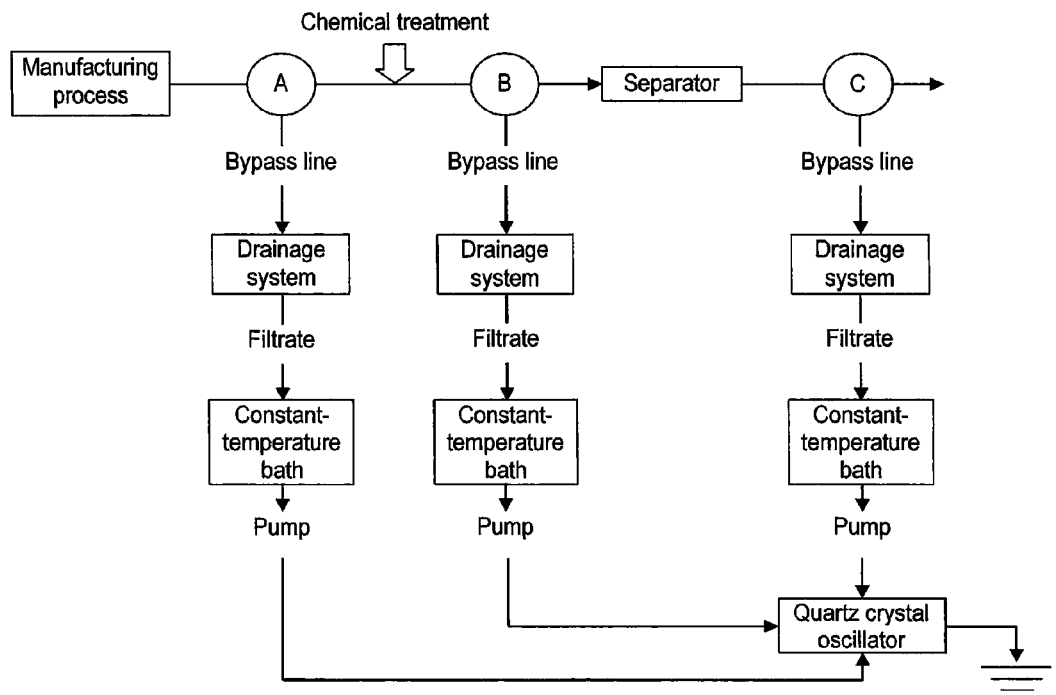
FIG. 12 is a flow chart of an on-line measurement of the present invention using a 4-channel molecular interaction analyzer incorporating on-line drainage systems.

The present invention may also include an on-line measurement according to a flow chart as shown in FIG. 11 incorporating the on-line drainage system described above. Further, the effect of a chemical treatment in a manufacturing process (comparison between A and B) and the effect of separation in a separator (comparison between B and C) can be determined at the same time by designing a flow chart as shown in FIG. 12 using an analyzer capable of measuring multiple samples at the same time by including multiple quartz crystal oscillators, such as a 4-channel molecular interaction analyzer (model Q-SENCE E4) from Q-sense.

For on-line observation of the morphology of deposits, a measuring cell with a glass window for the quartz crystal oscillator can be used to switch a test sample water to washing water at predetermined intervals and a digital microscope or the like can be used to capture an image of the deposits on the surface of the quartz crystal oscillator into a computer, whereby the morphology of the deposits can be quantified by image analysis as described above.

(Preparation Process of Paper)

In one embodiment, the present invention provides a process for preparing a paper. Thus, the present invention comprises determining susceptibility to deposition of a contaminant from a liquid or slurry in a manufacturing process of pulp and paper by the method described above. By determining deposition of a contaminant in this manner, the state of a papermaking system can be exactly known and the operating state can be optimized. Further, the present invention is advantageous in that paper breaks can be prevented or the operating efficiency can be improved by controlling the operating state by feedback control or the like on the basis of information from on-line measurement of deposition of the contaminant.

In a further preferred embodiment, the present invention comprises: determining deposition of a contaminant from a liquid or slurry in a manufacturing process of pulp and paper using a microbalance having a quartz crystal oscillator; and quantifying the morphology of deposits on the surface of the quartz crystal oscillator by image analysis; and further comprises adding a chemical for reducing deposition of the contaminant to the liquid or slurry; using a microbalance having a quartz crystal oscillator to determine the degree of deposition of the contaminant on the surface of the quartz crystal oscillator from the liquid or slurry after the chemical has been added; and then comparing the degree of deposition of the contaminant in the presence of the chemical with the degree of deposition of the contaminant in the absence of the chemical to evaluate the effect of the chemical, whereby a chemical effective against deposition of the contaminant can be selected. The papermaking efficiency can be greatly improved by carrying out such a procedure to select a chemical suitable for the papermaking system and preparing a paper while adding the selected chemical.

As used herein, chemicals for reducing deposition of contaminants are not specifically limited so far as they reduce deposition of contaminants from a liquid or slurry in manufacturing processes of pulp and paper, and generally include coagulants, retention aids, degrading agents, etc., specifically various polymers, enzymes, inorganic particles, etc. Preferred coagulants include relatively low molecular weight cationic polymers; retention aids include relatively high molecular weight cationic polymers; and degrading agents include enzymes, etc.

EXAMPLES

The following examples further illustrate the present invention without, however, limiting the invention thereto.

(Determination of the Degree of Deposition of Contaminants on a Quartz Crystal Oscillator [QCM Analysis])

A standard analysis method is described below, though the procedure for preparing samples and measurement conditions can be changed as appropriate depending on the composition or consistency of the stock. A molecular interaction analyzer (QCM-D300) from Q-sense was used for measurements in combination with a measuring sensor consisting of a quartz crystal oscillator coated with gold on the surface further having a polystyrene coating. This analysis method is hereinafter referred to as QCM analysis, and the degree of deposition of contaminants determined is referred to as QCM deposition. The quartz crystal oscillator is sometimes referred to as sensor.

A pulp slurry collected in a paper factory was adjusted to 0.5% and then filtered through a 500-mesh screen to give a filtrate. A 0.5 ml-aliquot of the filtrate was adjusted to a temperature of 25±0.5° C., and then introduced into a reaction cell and allowed to stand for 12 minutes while monitoring the amount of contaminants deposited on the surface of the quartz crystal oscillator as a change in oscillation frequency. After 12 minutes, the reaction cell was washed with distilled water for 3 minutes, and the amount deposited after washing was determined as QCM deposition. Thus, QCM deposition used herein refers to the amount of a substance deposited on the surface of a quartz crystal oscillator after it is adsorbed for 12 minutes from a liquid in contact with the surface followed by washing with water, and the change per unit time can provide information about the initial deposition rate of the substance.

Example 1

QCM Analysis of Samples from Various Process Stages

Figure 2:
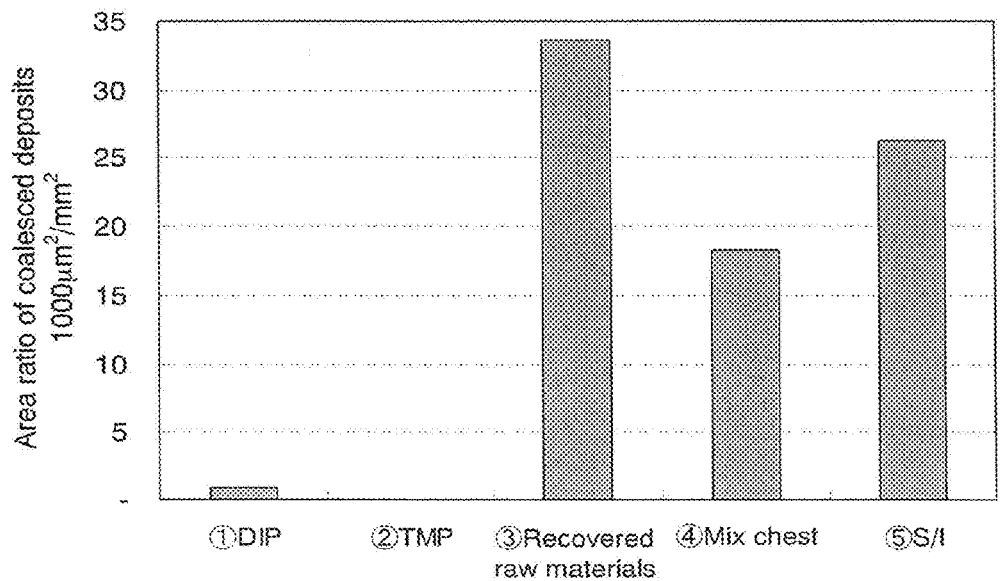
FIG. 2 is a graph showing the area ratio of coalesced deposits on the surface of a quartz crystal oscillator at various process stages.
Figure 3:
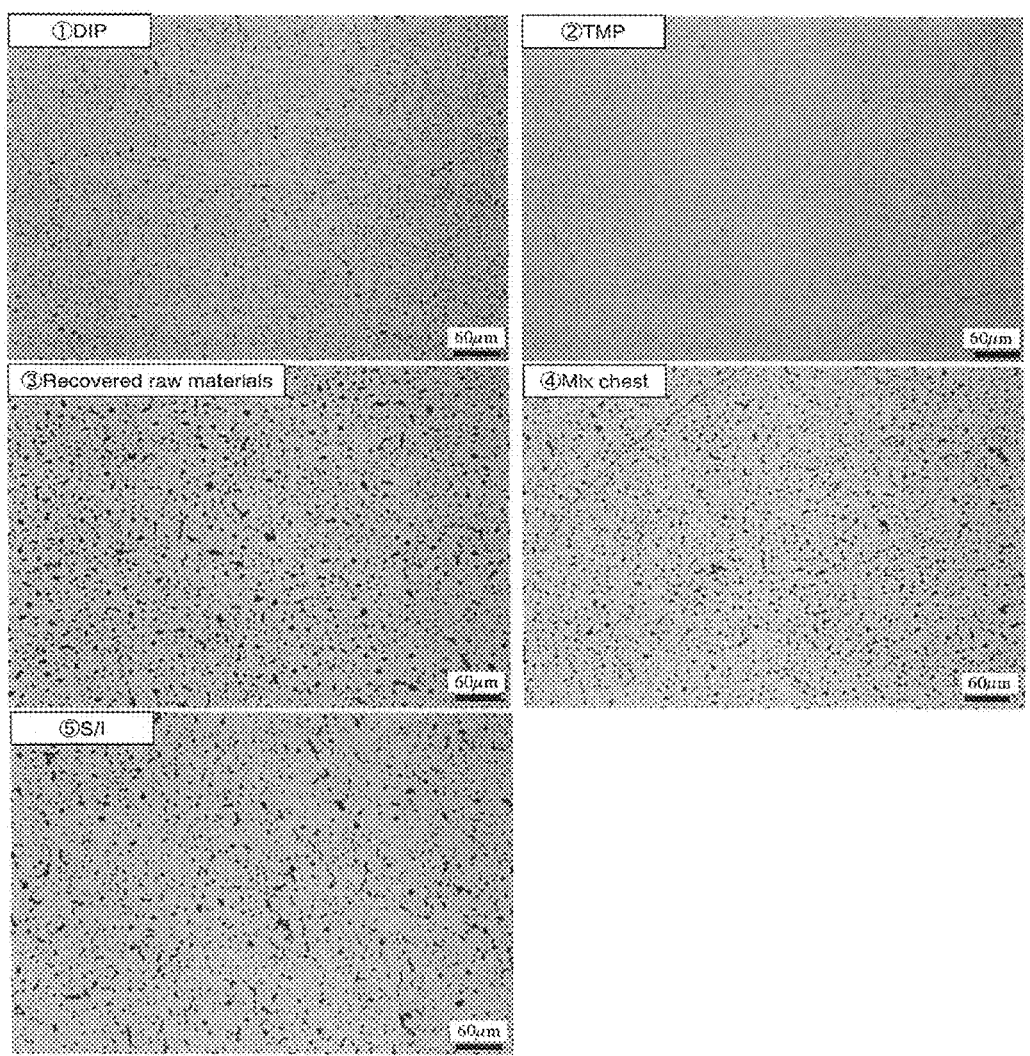
FIG. 3 is an image showing the appearance of the surface of a quartz crystal oscillator at various process stages.

In a gap former newsprint paper machine (ash content 15%, machine speed 1200 m/min) of paper factory A mainly using deinked pulp (DIP) and thermomechanical pulp (TMP) as raw materials, samples were collected at various process stages (1: finished DIP, 2: finished TMP, 3: raw materials recovered at the outlet of a white water recovery system, 4: mixing chest outlet, 5: stock inlet) and subjected to QCM analysis, and the results are shown in FIG. 1. Further, the area ratios of coalesced deposits of $\phi 6$ µm or more as determined by image analysis from images of the sensor surface after QCM analysis are shown in FIG. 2. A part of each image of the surface of the sensor obtained here is shown in FIG. 3.

Figure 4:
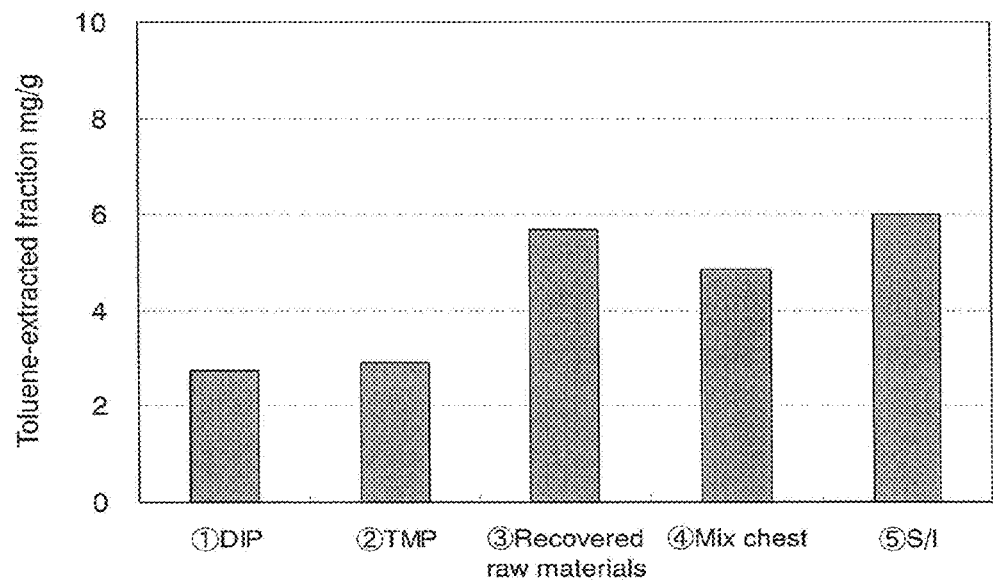
FIG. 4 is a graph showing the toluene-extracted fraction at various process stages (comparative example).

As a comparative example, the same samples as Example 1 were extracted with toluene, and the extracted fractions (mg/g) were determined from the solids weight before and after extraction. The results are shown in FIG. 4.

The results of Example 1 and comparative example show that the tendency of the toluene-extracted fractions and QCM deposition as well as the tendency of the area ratio of coalesced deposits vary. The toluene-extracted fractions are nearly comparable and low in DIP and TMP, and increase as the process advances to the mixing chest (Mix chest) and stock inlet (S/I). However, QCM deposition is low in TMP, and high in DIP, recovered raw materials and Mix chest, and somewhat low at S/I. Further, the area ratio of coalesced deposits shows that deposits are larger after post-treatments as compared with raw materials.

Further, it is shown that large amounts of sticky contaminants in DIP are deposited on the QCM sensor coated with hydrophobic polystyrene and that the deposits on the sensor surfaces are dispersed. It is also shown that the amount of pitch in TMP deposited on the QCM sensor is low in weight and that the deposits are very small and dispersed. Further, it is shown that the amount of deposits in recovered raw materials after the white water recovery system is comparable to DIP but the deposits are very large particles.

Generally, the weight of adhesives among organic fractions extracted with toluene is often approximately 10% and the remainder consists of oils/resins derived from inks and additive chemicals such as sizing agents, indicating that there is little correlation between the amount of extracted fractions per se and problems of sticky contaminants.

When determined from QCM deposition alone, the amount of deposits seems to decrease at S/I. When looking at the area ratio of coalesced deposits as proposed by the present invention, however, it is presumed that contaminants per se are agglomerated/coalesced and deposited though the degree of deposition of the contaminants decreases by the addition of cationic chemicals or the like during the papermaking process. It is also shown that contaminants in recovered raw materials after the white water recovery system are very large. Further, the actual morphology can be identified as shown in FIG. 3. Thus, the present invention allows more exact evaluation of deposits contained in a liquid or slurry in a manufacturing process of pulp and paper than previously.

Example 2

Analysis in Various Treatments in the DIP Process

Figure 5:
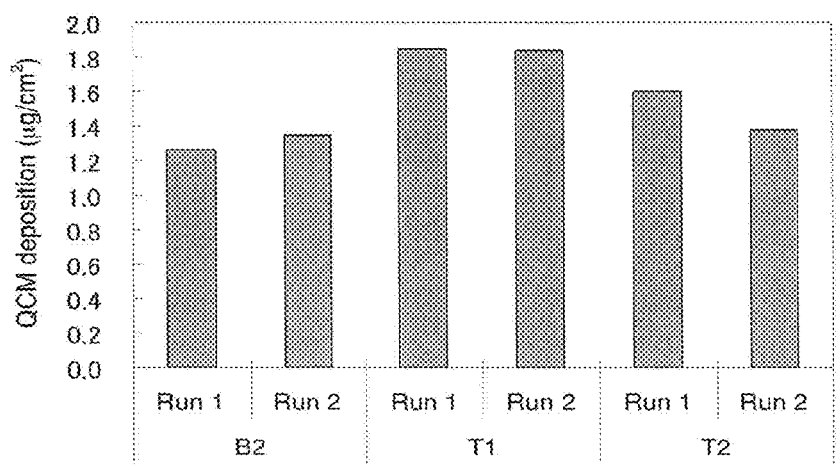
FIG. 5 is a graph showing the degree of deposition of contaminants on a quartz crystal oscillator after various treatments in the DIP process.

In the DIP process of paper factory B, a coagulant treatment (T1) and an enzyme treatment (T2) were performed in contrast to normal treatment (B2), and the results are shown in FIG. 5 (each in duplicate). In the coagulant treatment, 100 ppm of Catiofast SF (modified polyethyleneimine) from BASF was added to the finished DIP and then samples were collected at the inlet of the mixing box of the paper machine and used for QCM analysis. In the enzyme treatment, 100 ppm of Optimize 525 (sticky contaminant-degrading enzyme) from Buckman Laboratories International, Inc. was added to the finished DIP and then samples were collected at the inlet of the mixing box of the paper machine and analyzed in the same manner. As a control (normal treatment), DIP samples without any chemical added were collected at the mixing box and analyzed in the same manner.

Figure 6:
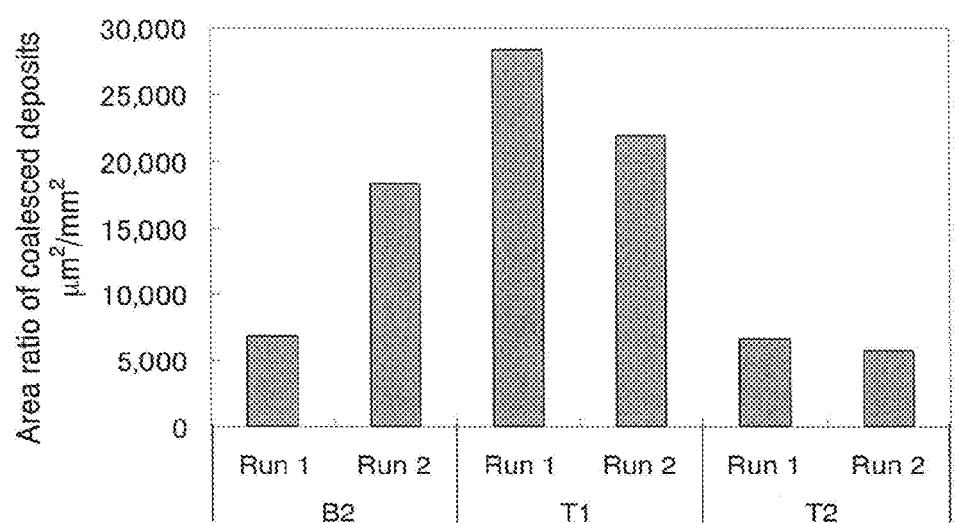
FIG. 6 is a graph showing the area ratio of coalesced deposits on the surface of a quartz crystal oscillator after various treatments in the DIP process.
Figure 7:
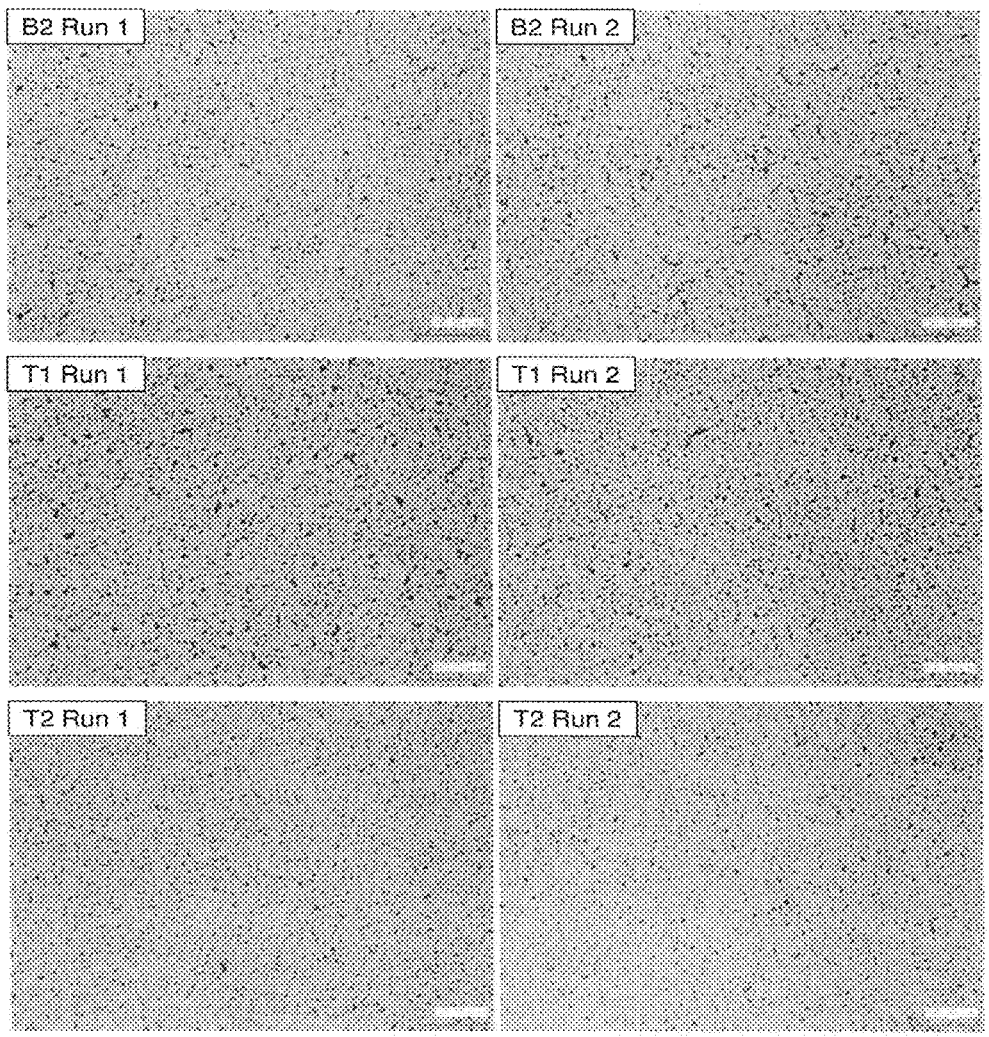
FIG. 7 is an image showing the appearance of the surface of a quartz crystal oscillator after various treatments in the DIP process. The scale is the same as used in FIG. 3.

The area ratio of coalesced deposits having a particle size of 6 µm or more was determined from images of the surface of the sensor after analysis and the results are shown in FIG. 6. Further, the images obtained here are shown in FIG. 7.

As shown from these results, QCM analysis judges that both coagulant treatment (T1) and enzyme treatment (T2) have no effect as compared with normal treatment (B2), but coupled to the area ratio of coalesced deposits according to the method of the present invention, T1 has an adverse effect in terms of the runnability of the paper machine because agglomeration of contaminants is promoted while T2 has a good effect in terms of the runnability of the paper machine because contaminants are dispersed.

Example 3

Figure 8:
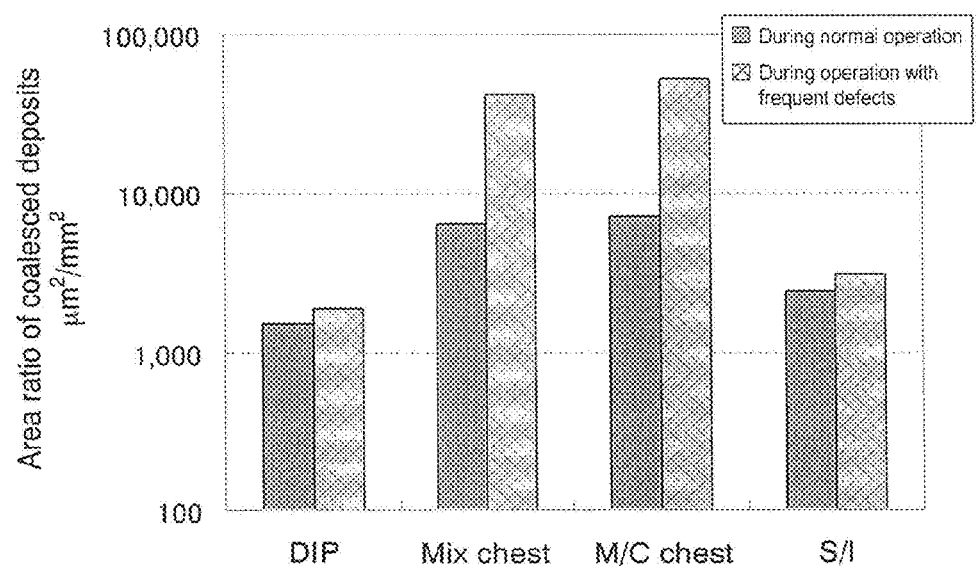
FIG. 8 is a graph showing the area ratio of coalesced deposits on the surface of a quartz crystal oscillator during normal operation and during operation with frequent defects.
Figure 9:
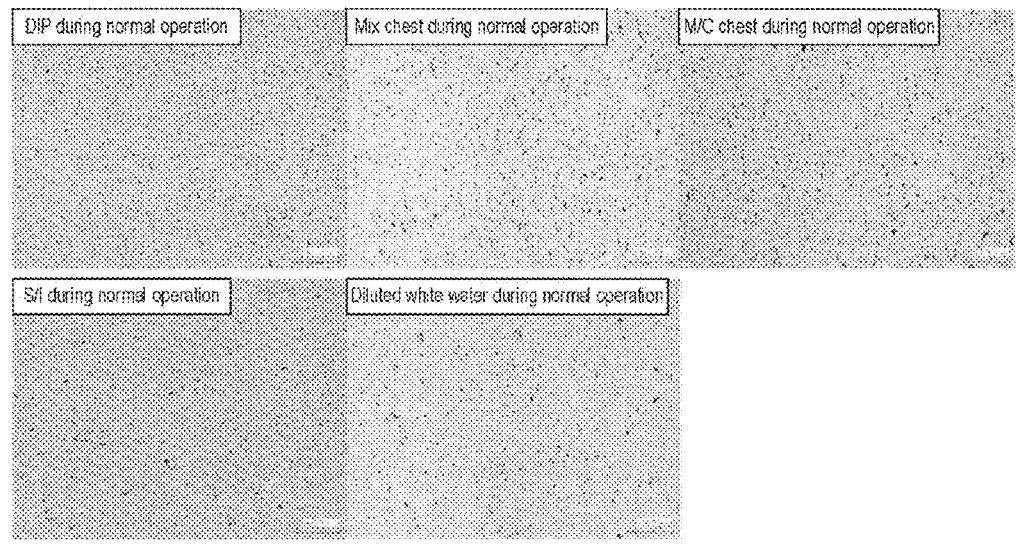
FIG. 9 is an image showing the appearance of the surface of a quartz crystal oscillator during normal operation. The scale is the same as used in FIG. 3.
Figure 10:
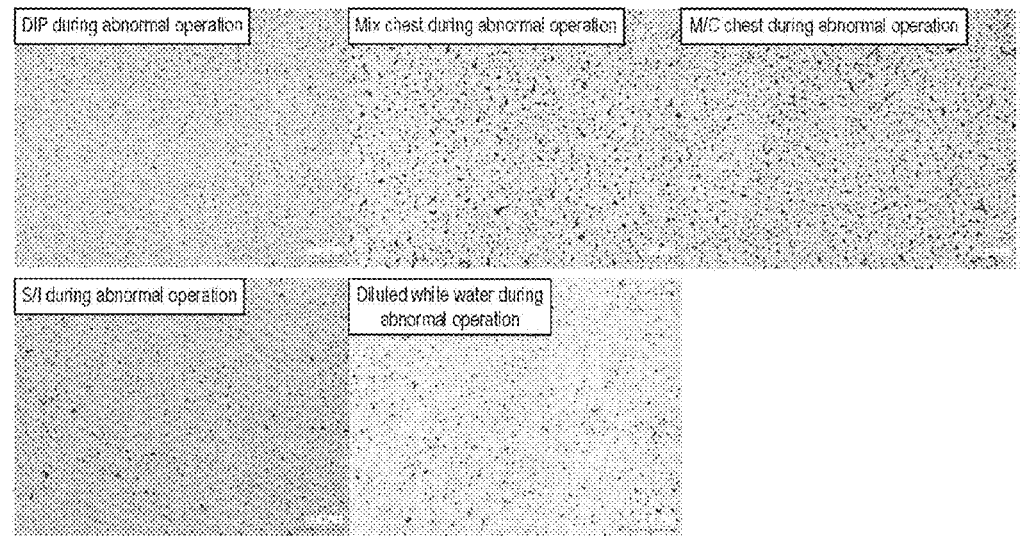
FIG. 10 is an image showing the appearance of the surface of a quartz crystal oscillator during operation with frequent defects. The scale is the same as used in FIG. 3.

Determination During Normal Operation and During Operation with Frequent Defects In a gap former newsprint paper machine (DIP 100%, ash content 12%, machine speed 1250 m/min) of paper factory A, process samples during normal operation and during operation with frequent defects were collected and subjected to QCM analysis. Further, the area ratios of coalesced deposits of ϕ6 μm or more as determined by image analysis from images of the sensor surface after QCM analysis are shown in FIG. 8. A part of each image of the surface of the sensor obtained here is shown in FIG. 9 and FIG. 10. It should be noted that the number of defects during normal operation was 16 defects/hr, while the number of defects during operation with frequent defects was 300 defects/hr. As shown in FIG. 8, the situation in which paper defects occur tends to be worsened when the area ratio of deposits having a predetermined size or more is high, showing that the state of the papermaking system can be exactly known by the present invention.

The invention claimed is:

1. A method for determining deposition of a contaminant from a liquid or slurry in a manufacturing process of pulp and paper, which comprises:
 using a microbalance having a quartz crystal oscillator, a surface of which is coated with a material having a solid surface free energy of 75 mJ/m² or less, to determine the degree of deposition of the contaminant from the liquid or slurry on the quartz crystal oscillator; and
 quantifying the morphology of deposits on the surface of the quartz crystal oscillator by image analysis,
 wherein the quantifying step comprises quantifying the proportion of deposits having a particle size equal to or more than a predetermined number from 3 to 20 micrometer.

2. The method of claim 1, wherein the surface of the quartz crystal oscillator is coated with an organic material.

3. The method of claim 1, wherein the surface of the quartz crystal oscillator is coated with a material having a solid surface free energy of from 30 to 40 mJ/m².

4. The method of claim 1, wherein the contaminant is a substance containing a hydrophobic organic matter.

5. The method of claim 1, wherein the contaminant is a sticky contaminant.

6. The method of claim 1, wherein the contaminant is pitch.

7. The method of claim 1, which further comprises:
 adding a chemical for reducing deposition of the contaminant to the liquid or slurry;
 using a microbalance having a quartz crystal oscillator to determine the degree of deposition of the contaminant on the surface of the quartz crystal oscillator from the liquid or slurry after the chemical has been added; and
 comparing the degree of deposition of the contaminant in the presence of the chemical with the degree of deposition of the contaminant in the absence of the chemical to evaluate the effect of the chemical.

8. The method of claim 1, which comprises using multiple quartz crystal oscillators coated with different materials on their surfaces to determine deposition of the contaminant from the liquid or slurry.

9. The method of claim 1, which is an on-line continuous measurement.

10. A process for preparing a paper, comprising the method of claim 1.

11. The method of claim 2, wherein the surface of the quartz crystal oscillator is coated with a material having a solid surface free energy of from 30 to 40 mJ/m².

* * * * *